(12) United States Patent
Umbrage et al.

(10) Patent No.: US 12,270,801 B2
(45) Date of Patent: *Apr. 8, 2025

(54) SYSTEM AND METHOD FOR MONITORING AND CLASSIFYING SMOKING EVENTS IN MONITORED SPACES

(71) Applicant: NoiseAware Inc., Dallas, TX (US)

(72) Inventors: Jacob Umbrage, Dallas, TX (US); Almog Boanos, Dallas, TX (US); Andrew Schulz, Dallas, TX (US)

(73) Assignee: NoiseAware Inc., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/260,766

(22) PCT Filed: Oct. 28, 2022

(86) PCT No.: PCT/US2022/048278
§ 371 (c)(1),
(2) Date: Jul. 7, 2023

(87) PCT Pub. No.: WO2023/076627
PCT Pub. Date: May 4, 2023

(65) Prior Publication Data
US 2024/0060948 A1  Feb. 22, 2024

Related U.S. Application Data

(60) Provisional application No. 63/272,988, filed on Oct. 28, 2021.

(51) Int. Cl.
*G01N 33/00* (2006.01)
*F24F 110/62* (2018.01)
*G05B 19/048* (2006.01)

(52) U.S. Cl.
CPC ....... *G01N 33/0075* (2013.01); *G05B 19/048* (2013.01); *F24F 2110/62* (2018.01)

(58) Field of Classification Search
CPC .............. G01N 33/0075; G05B 19/048; F24F 2110/62
(Continued)

(56) References Cited

U.S. PATENT DOCUMENTS 6,111,512 A    8/2000  Sugimoto et al.
6,711,470 B1 * 3/2004  Hartenstein .............. F24F 11/74
                                                  700/266
(Continued)

OTHER PUBLICATIONS

F. Nelson, et al. "A multipollutant smoke emission sensing—development and testing", MDPI, Jun. 7, 2019 (Year: 2019).*

*Primary Examiner* — Md Azad (57) ABSTRACT

A system, method, and apparatus are provided with features that allow hosts to be alerted of risks to the well-being of their space that may arise, for example, from a breach of contract, violation of local laws, or violation of established property rules. In one example an air analyzer is provided that includes: (1) multiple sensors including one or more of a digital multi-pixel gas sensor, a digital humidity and temperature sensor, or a particulate matter sensor, wherein each of the multiple sensors is configured to obtain a sample of air and derive therefrom an environmental attribute, wherein the environmental attributes provide a signature of the sampled air, and (2) a smoke classifier configured to classify a smoking event by comparing the signature of sampled air to signatures of a classification model.

27 Claims, 4 Drawing Sheets

(58) Field of Classification Search
USPC .......................................................... 700/276
See application file for complete search history.

(56) References Cited

U.S. PATENT DOCUMENTS

| | | | |
|---|---|---|---|
| 10,403,118 B2* | 9/2019 | Schulz | H04R 29/00 |
| 2003/0004426 A1* | 1/2003 | Melker | G01N 29/4427 |
| | | | 422/84 |
| 2006/0173580 A1* | 8/2006 | Desrochers | G01N 33/0075 |
| | | | 73/31.01 |
| 2015/0096352 A1 | 4/2015 | Peterson et al. | |
| 2015/0097678 A1 | 4/2015 | Sloo et al. | |
| 2015/0097682 A1 | 4/2015 | Rossi et al. | |
| 2015/0097689 A1 | 4/2015 | Logue et al. | |
| 2016/0343227 A1 | 11/2016 | Shih et al. | |
| 2018/0073759 A1* | 3/2018 | Zhang | F24F 11/30 |
| 2018/0115788 A1 | 4/2018 | Burns et al. | |
| 2018/0119973 A1 | 5/2018 | Rothman et al. | |
| 2018/0350220 A1 | 12/2018 | Gonzales | |
| 2021/0071894 A1* | 3/2021 | Nigg | G08C 17/02 |

* cited by examiner

SYSTEM AND METHOD FOR MONITORING AND CLASSIFYING SMOKING EVENTS IN MONITORED SPACES

CROSS-REFERENCE TO RELATED APPLICATION

This application is the National Stage of, and therefore claims the benefit of, International Application No. PCT/US2022/048278 filed on Oct. 28, 2022, entitled "SYSTEM AND METHOD FOR MONITORING AND CLASSIFYING SMOKING EVENTS IN MONITORED SPACES," which claims the benefit of U.S. Provisional Application Ser. No. 63/272,988, filed by Jacob Umbrage, et al. on Oct. 28, 2021, entitled "SYSTEM AND METHOD FOR MONITORING AND CLASSIFYING COMBUSTIBLE OR VAPORIZED NICOTINE AND MARIJUANA," both which are commonly assigned with this application and incorporated herein by reference in their entirety.

TECHNICAL FIELD

The disclosure relates generally to analyzing air in an environment and, more specifically, to detecting smoking events in the environment.

BACKGROUND

The hospitality and travel industry enable people to rent rooms, cars, and properties on a temporary basis, referred to from here on out as spaces. Despite a long history of industry success, these spaces continue to be used in ways that violate the original terms of the rental contract. Additionally, the terms of use of the rental contract have created substantial angst over privacy and freedom to contract and has led to alleged discriminatory practices by hosts that have raised fair housing concerns. The industry also suffers since financial, tax, and legal liabilities have yet to be fully settled among hosts and guests. Nevertheless, the violation of these contracts often results in the owner of the space being financially responsible to rectify the situation.

For example, an issue that has garnered attention in the media has been misuse incidents of spaces that have been rented. Stories of property damage, vandalism or theft resulting from over occupancy or immoderate parties, noise complaints from loud music, and smoking continue to be reported by the media. The smoking instances often lead to, for example, long term damage of brand, damage of soft goods and linens, additional cleaning costs, additional labor costs, and loss of revenue as spaces are taken out of circuit for cleaning.

SUMMARY

In one aspect the disclosure provides an air analyzer. In one example the air analyzer includes: (1) multiple sensors including one or more of a digital multi-pixel gas sensor, a digital humidity and temperature sensor, or a particulate matter sensor, wherein each of the multiple sensors is configured to obtain a sample of air and derive therefrom an environmental attribute, wherein the environmental attributes provide a signature of the sampled air, and (2) a smoke classifier configured to classify a smoking event by comparing the signature of sampled air to signatures of a classification model.

In another aspect, the disclosure provides a method of detecting smoking events. In one example, the method includes: (1) sampling air using one or more sensors, (2) determining presence of a trigger event and a termination event from the sampled air, (3) determining one or more smoking events by comparing the time window between the trigger and termination events to time windows of modelled smoking events, (4) comparing the representations of the sampled air with signature models for the determined smoking events, and (5) classifying a smoking event based on the comparing.

In yet another aspect, the disclosure provides an analysis/response engine. In one example the analysis report engine includes: (1) a communications interface couplable to a network and configured to receive therefrom at least one smoke classification from an air analyzer, (2) a smoke classification evaluator associated with a host database and configured to evaluate said at least one smoke classification using data from said host database to determine if said at least one smoke classification should merit a response, and (3) a transmitter, associated with said smoke classification evaluator and configured to issue the response.

In still another aspect, the disclosure provides another example of an air analyzer. In this example, the air analyzer includes: (1) one or more sensors configured to identify environmental attributes in air proximate the air analyzer, and (2) a classifier configured to determine a smoke event based on the environmental attributes.

BRIEF DESCRIPTION

The present invention is illustrated by way of example and not limitation in the figures of the accompanying drawings in which like references indicate similar elements.

DETAILED DESCRIPTION

As stated above, property owners of rented spaces have been forced to deal with, and often pay for property damage, cleaning, fines, and the damaging effects to brand image from customers smoking in the rental spaces. It is realized herein that unusual or particular patterns of smoke typically lead to these destructive, harmful, and sometimes illegal behaviors and that detection and classification of these smoking events could prove valuable in intercepting and bringing to a halt such behaviors. It is further realized herein that bringing a halt to such behaviors may include notifying responsible persons, host, authorities, other interested parties, or a combination thereof.

Introduced herein are examples of systems, methods, and apparatuses having features for generating responses based on one or more smoke classifications that may prevent or at least mitigate the damaging effects of smoke (e.g., nicotine and marijuana) to a monitored space. The disclosed features allow hosts to be alerted of risks to the well-being of their space that may arise, for example, from a breach of contract, violation of local laws, or violation of established property rules.

In one example, an air analyzer is disclosed that includes one or more sensors that are used to identify environmental attributes in air and a smoke classifier that determines a smoking event based on the environmental attributes. The air analyzer can include multiple sensors, including different types of sensors, for identifying the environmental attributes. Environmental attributes are different physical properties of air determined by one or more sensors from air sampled by the one or more sensors. The various sensors can be conventional sensors, such as digital sensors, that generate an analog to digital (ADC) signal or offset reading that is sent to the smoke classifier. The output of the one or more sensors is raw data that represents the environmental attributes and is processed by the smoke classifier, which includes comparing to models for classification. For example, the air analyzer can include a particulate matter sensor, a temperature and humidity sensor, and a pixel gas sensor. The raw data from the sensors is provided to a processor of the smoke classifier that executes an advanced classification model built from the observations of samples. The classification model is designed to identify the unique fingerprints of these different smoking events from momentary snapshots of time, as sampled by the one or more sensors. Based on the model developed from samples, the processor will make an approximation of high likelihood of the type of smoking event that is occurring.

These smoking classifications can then be transmitted, e.g. wirelessly, through a network to an analysis/response engine, where it is used, perhaps in the aggregate with other classification events, to determine if a response should be initiated. A response can be one or more alerts that are generated, one or more actions that are initiated, or a combination of both. The type of disturbance that has occurred can also be characterized and reported with an alert. Other classification events that can be used with the smoking classification can be based on, for example, noise.

In addition to responses based on classifications, other types of responses can be initiated based on, for example, loss of power of the air analyzer, loss of connection of a wireless network, or other operational problems. Hosts can set up how responses are handled. For example, hosts or managers designated by hosts can set up who receives alerts and can set up particular actions to take. Alerts may be routed to delegated parties via various means including, Short Message Service (SMS), electronic mail, push notifications, phone calls, and a combination thereof. The air analyzer can include a speaker that may generate a sound to provide an audible warning as an alert at the monitored space. An alert can also be sent to the monitored space, such as to a television, computing device, intercom system, alarm system, automobile horn, etc., wherein an alert that is visible, audible, or both is provided within the monitored space.

Property owners of various spaces, referred to hereinafter as owners, can use a World Wide Web portal to set up personal tolerances for what is acceptable for a given space. This can include a sensitivity threshold for tuning the classification model against false positives or false negatives and a selection of what smoking events the owners care about, e.g., E-cigarettes, marijuana, and combustible nicotine. As such, an owner or manager can prioritize the smoking events they are the most concerned about and also dictate when to initiate responses, such as when to generate alerts, how the alerts will be sent, and to whom or what device or devices the alerts will be sent.

In addition to one or more sensors for analyzing air, the air analyzer may include other environmental sensors or be used with other types of sensors, such as: vibration sensor, wireless network signals, barometric pressure, temperature, light detection, and motion detection. The air analyzer can be a stand-alone device or can be integrated with another type of device designated for another purpose, such as a thermostat, a fire alarm, a carbon monoxide detector, and a noise detector.

Figure 1:
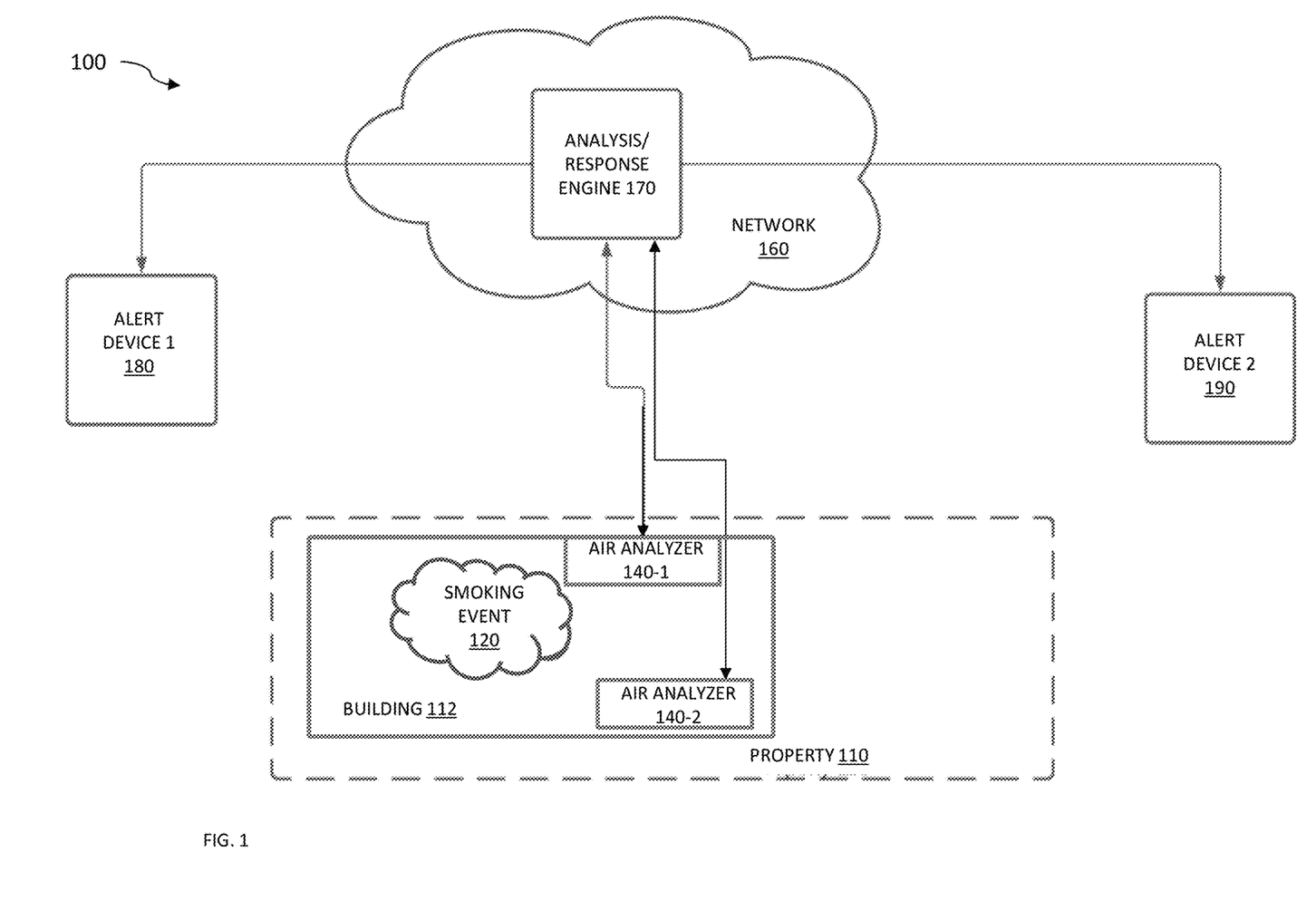
FIG. 1 is a high-level diagram of an example of a system for classifying smoking events based on type and severity in an example operating environment.

FIG. 1 is a high-level diagram of an example of a monitoring system 100 for initiating a response based on smoking events located in an example operating environment. In FIG. 1, the operating environment includes a property 110 having a building 112 located thereon. The building 112 represents a monitored space, which is a space having at least one air analyzer as disclosed herein. In an example, the building 112 is a single-family home. In another example, the building 112 is a multiple-family home. In yet another example, the building 112 is an apartment or condominium that is part of a larger structure. In still another example, the building 112 is a room, suite or apartment in a dormitory, hotel, hospital, rehabilitation center, long-term care center or skilled nursing facility. In yet still another example, the building 112 is a commercial or industrial space, such as a storefront, warehouse or factory. Those skilled in the art will readily see that the building 112 represents any structure within any space in or at which detection of smoking events may be needed or desired. As such, the building 112 may be an automobile, such as a rental car, van, truck or any other classification of a motorized vehicle.

FIG. 1 specifically illustrates a situation, purely for purposes of discussion, in which the monitored space has one occurring smoking event 120 associated with it. In other words, one source of damaging or potential damaging smoking is within the building 112.

The property 110 is illustrated as having at least one air analyzer associated with it. In FIG. 1, two air analyzers 140-1, 140-2, are located in or around the building 112. One air analyzer, e.g. the air analyzer 140-1 or the air analyzer 140-2, may be sufficient to provide smoking event detection, but, as will be understood, multiple air analyzers can be advantageously employed in some monitored spaces. Each air analyzer 140-1, 140-2, is coupled directly or indirectly to a network 160. The network 160 is a communications network, represented in FIG. 1 as a "cloud" that includes data processing, storage and communication hardware and software, as is familiar to those skilled in the pertinent art. The network 160 can include one or more conventional networks used for local or distal communication of data.

An analysis/response engine 170 is coupled to or within the network 160 for communication therewith. The analysis/response engine 170 is further coupled to at least one alert device. FIG. 1 shows, as an example, two alert devices: alert device 1 180 and alert device 2 190. In the illustrated example, at least one of the alert device 1 180 and the alert device 2 190 is a mobile device, e.g., a smartphone. The alert may take the form of a telephone call, an electronic mail message, a text message or any other form of alert suitable to warn a host or another designated party of a noise risk with respect to the monitored space, building 112. The alert may indicate the existence of a smoking risk, without more. Upon receipt of an alert, the host can take various steps to abate the smoking event, including contacting the guest, contacting neighbors, contacting a leasing agent, or contacting the authorities. Alternatively, the host may ignore the alert. Additionally, an alert can be automatically sent to the various parties for abatement such that the host does not have to contact them. In addition to or instead of generating an alert, another response to abate the smoking event can include initiating an action, such as operating an HVAC system, operating a fan, or opening a window at the building 112. These actions can be initiated by the host or can be automatically initiated by the analysis/response engine 170. As such, the analysis/response engine 170 can be communicatively coupled to one or more devices (i.e., abatement devices) of the building 112 that can be automatically operated for abatement of smoking event 120. The connections for the communication can be via a transceiver of one of the air analyzers 140-1, 140-2 and may include a local area network of the building 112.

As noted above, an alert may be dispatched by the analysis/response engine 170 to the guest to warn the guest to desist from smoking activities. The guest may be warned by the host according to multiple thresholds, such as, a lower one to trigger a guest warning, and a higher one to trigger a host warning. This stratified scheme gives the guest an opportunity to correct behavior before stronger measures are taken, such as contacting the host, the authorities, or initiating an action for abatement.

In operation, the air analyzers 140-1, 140-2 are configured to provide smoke classifications over time and transmit them directly, via each other, and/or via network 160 to the analysis/response engine 170. The analysis/response engine 170 is configured to determine, based at least in part on the smoke classifications, whether and when to initiate a response, such as when to generate alerts and the alert device to which to send given alerts. Evaluation of the smoke classifications may involve smoke classifications from one other smoke detector or smoke classifications from multiple smoke detectors and classifiers, analyzed in concert to gain additional insight. For example, air analyzer 140-1 may generate a smoke classification of a type of nicotine event and air analyzer 140-2 may not generate such a smoke classification. The analysis/response engine 170 can consider the lack of smoke classification (or a different one) from air analyzer 140-2 and wait until initiating a response. In certain monitored spaces, air analyzers such as air analyzers 140-1, 140-2, may be readily visible to encourage vigilance with respect to smoking and may include visual and audible devices, such as flashing lights or speakers to provide alerts directly to guests. Air analyzer 200 of FIG. 2, for example, includes a display 294 and a speaker 298.

Figure 2:
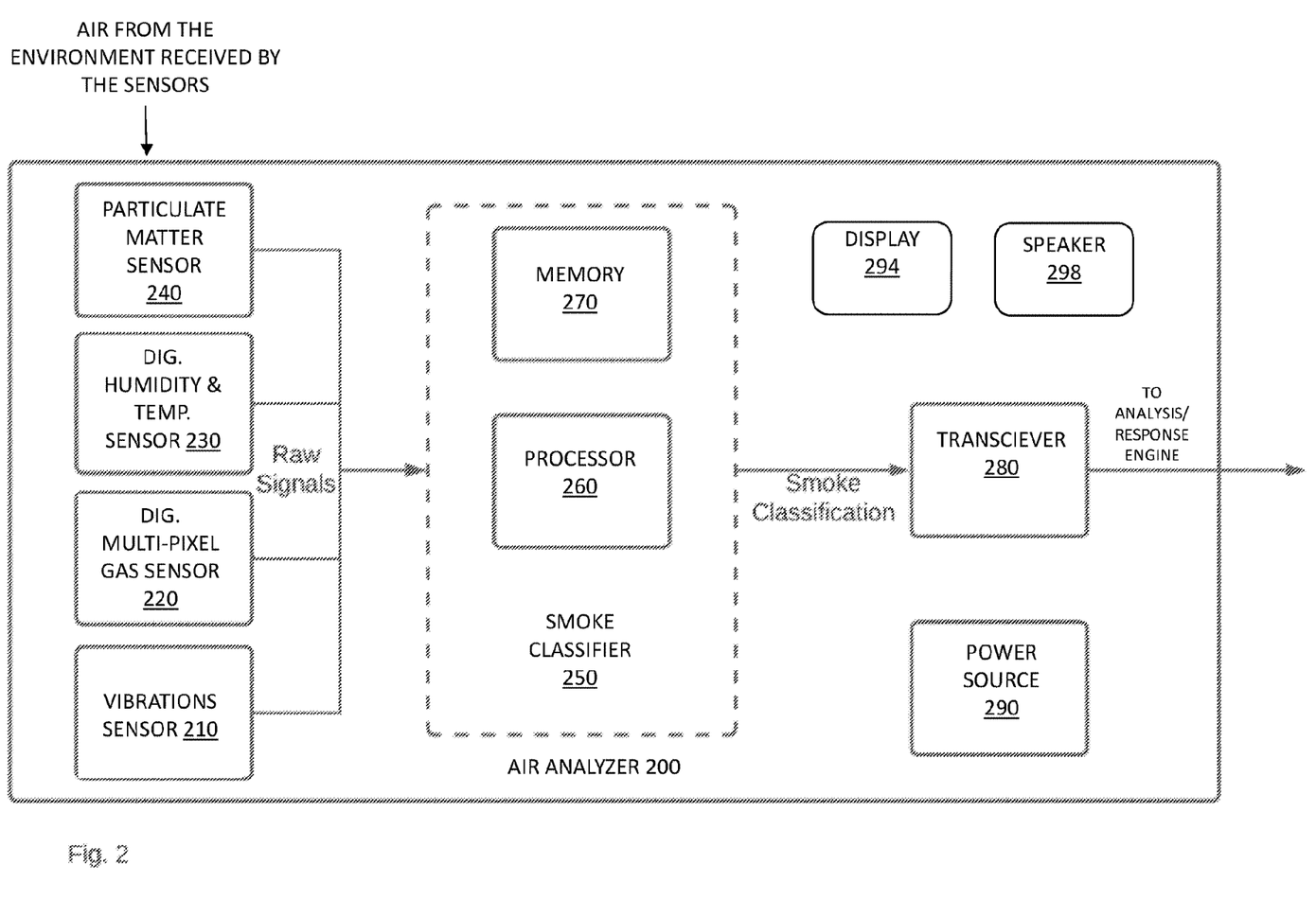
FIG. 2 is a block diagram of an example of an air analyzer constructed according to the principles of the disclosure.

FIG. 2 is a block diagram of an example of an air analyzer 200 (e.g., the air analyzer 140-1 and 140-2 of FIG. 1). The illustrated example of the air analyzer 200 includes a vibration sensor 210, a digital multi-pixel gas sensor 220, a digital humidity and temperature sensor 230, and a particulate matter sensor 240. The vibration sensor 210 is configured to derive a raw signal from noise proximate to the air analyzer 200 and the digital multi-pixel gas sensor 220 is configured to measure organic compounds, such as total volatile organic compounds (TVOC) and carbon dioxide ($CO_2$). Nitrogen oxides (NOX) can also be measured. As such, the digital multi-pixel gas sensor 220 can perceive levels of CO2, TVOC, and NOX. The digital humidity and temperature sensor 230 is configured to measure base temperature and humidity of the environment proximate the air analyzer 200 and the particulate matter sensor 240 is configured to measure particulates in the environment proximate the air analyzer 200. The particulate matter sensor 240 can, for example, measure concentration and mass across multiple unique bins and average particulate counts. Various binning methods can be employed including using the max and min of bins. For example, the number of unique bins can be nine.

The sensors 210, 220, 230, 240, can be conventional sensors. In other examples, the number of sensors or the type of sensors can vary.

The air analyzer 200 also includes a smoke classifier 250 having a one or more processor, represented by processor 260 and one or more memory, represented by memory 270. The smoke classifier 250 is coupled to vibration sensor 210, digital multi-pixel gas sensor 220, digital humidity and temperature sensor 230, and particulate matter sensor 240, and is configured to receive a raw signal output from the different sensors. The vibration sensor 210 is configured to derive a raw signal from noise proximate to the air analyzer 140. The raw signal from the other sensors can be based on the measurements that are obtained by the individual sensors. For example, the digital multi-pixel gas sensor 220 is configured to measure TVOC and Co2, the digital humidity and temperature sensor 230 is configured to measure base temperature and humidity of the environment, the particulate matter sensor 240 is configured to determine particulates in the environment. A nitrogen oxide sensor is another example of a sensor that can be used in the air analyzer 200. The raw signals represent the environmental attributes of the air determined by the sensors. Components of the air analyzer 200 can be connected via connections typically employed in electronic devices.

The smoke classifier 250 is a predictive model built off of quantities of samples, such as large quantities of samples, taken from various spaces to finger print and classify different smoking events. Machine learning or artificial intelligence (AI) can be used for the smoke classifier 250. For example, unsupervised, supervised, or reinforcement learning may be used. A neural network or a boosted decision tree are examples of different implementations that can be used for the smoke classifier 250. For a supervised system, feedback can be received from users to improve the model for classifying. For example, hosts can confirm the occurrence or non-occurrence of smoking events and this input can be used to update the model used by the smoke classifier 250 by relabeling signatures (i.e., datasets).

The smoke classifier 250 can classify all smoking events as simply one type of smoking event, such as a "smoke" event. The smoke classifier 250 can also classify events as unique individual events e.g. cigarette, marijuana, vape, cigar, or pipe. The smoke classifier 250 may also classify further smoking events of other combustible recreational substances or high temperature vaporized recreational substances that are legal or illegal. As such, the smoke classifier 250 can be used to classify smoking events associated with legal substances, illegal substances, or a combination of both. Accordingly, the smoke classifier 250 can identify when illegal and legal substances are being smoked based on corresponding signatures.

The processor 260 is further configured to generate a time stamp and an identifying number corresponding to the air analyzer 200. The time stamp indicates the time to which the smoking event pertains, and the identifying number indicates the particular air analyzer. The identifying number, or air analyzer ID, differentiates the smoke type detected by one air analyzer from those generated by another air analyzer and can be used to identify a host for alerting and checking of applicable host preferences/priorities.

The memory 270 can store signatures, samples, data, etc. that are used by the processor 260 for classifying. The memory 270 can be a non-transitory memory. The memory 270 can also include a series of operating instruction corresponding to one or more algorithms that direct operation of the processor 260 when executed thereby to process the received raw signals to develop a signature therefrom and compare the processed signature to stored signatures. The stored signatures can correspond to unique readings from time windows that represent different smoking events. Different time windows can be identified with different smoking events. For example, a time window of 3-5 seconds can correspond to a person exhaling smoke from a cigarette. The time when the sensors produce raw signals indicating a start of a smoking event, a trigger, and the time when the measurements subside, a termination, are noted. The processor 260 can then compare the measurements (e.g., raw signals or processed raw signals) to signatures of smoking events of similar or same duration and also compare the measurements. Based on the comparison, the processor 260 can provide a smoking event classification. The trigger can be based on thresholds that can be predetermined. The termination can be based on the sensors 210, 220, 230, 240, returning to their baseline. Different thresholds can be used for different smoking events and can be dynamically adjusted based on feedback. Signatures can also be adjusted based on additional samples and fine tuning of the signatures for specific locations can be performed. Multiple samples can be collected and used to derive the signatures for future use and modelling. Feedback, such as from hosts, can be used for updating the stored signatures for modelling.

The illustrated example of the air analyzer 200 further includes a transceiver 280. The transceiver 280 is coupled to the smoke classifier 250 and is configured to transmit the smoke classification to a network (e.g., the network 160 of FIG. 1). The transceiver 280 can communicate using a standard protocol typically used in the industry. For example, the transceiver 280 can be a compliant transceiver selected from the group consisting of: WiFi, cell (e.g., GSM, CDMA), Zigbee/Zwave, mesh, Low Power, Wide Area, LoRa®, LPWAN, power line, infrared and ultrasonic capable transceivers. The transceiver 280 can also receive updates, such as software updates for the processor 260 to execute and/or updates on signatures for modelling that can be stored on the memory 270. The transceiver 280 is typically wireless but can also have wired capability, especially for updates. The transceiver 280 can also send operating commands to abatement devices within a monitored space. The operating commands can be received from an analysis/response engine to initiate an action. A local area network can be used to communicate the operating commands to the abatement devices.

The air analyzer 200 further includes a power source 290 coupled to the smoke classifier 250 and the transceiver 280. The power source 290 can be or can include a battery. Other conventional or later-developed power sources can also be employed. The power source 290 can include a power converter configured to convert power to a voltage appropriate for the air analyzer 200. The latter example allows the air analyzer 200 to be plugged into a standard power outlet. The air analyzer 200 also includes a display 294 and a speaker 298 that can be used to provide visible and audible alerts directly to guests. The display can be a light. The audible alerts can be spoken words, an alarm, or a combination of both. The spoken words can be specific for the type of smoking event that is classified.

As stated above, smoke classifications from multiple smoke detectors and classifiers may be transmitted to an analysis/response engine that analyzes the smoke classification to determine whether a response is merited, such as initiating an action or generating an alert and determining one or more destinations of any alerts that may be generated. One air analyzer can be used to send data/information from one or more other air analyzers to the analysis/response engine. For example, air analyzer 140-1 can send classification information for both 140-1 and 140-2. The air analyzer 200 can send data even when no classification of a smoking event was determined. The data can include the raw data from the sensors that can be stored and used for developing signatures. All readings from the sensors 210, 220, 230, 240, can be sent and stored in a memory, such as a memory of the analysis/response engine for analysis and processing. The air analyzer 200 can also send the raw data with the smoke classifications. In some examples, the air analyzer 200 may only transmit information when a smoke classification has been determined.

Figure 3:
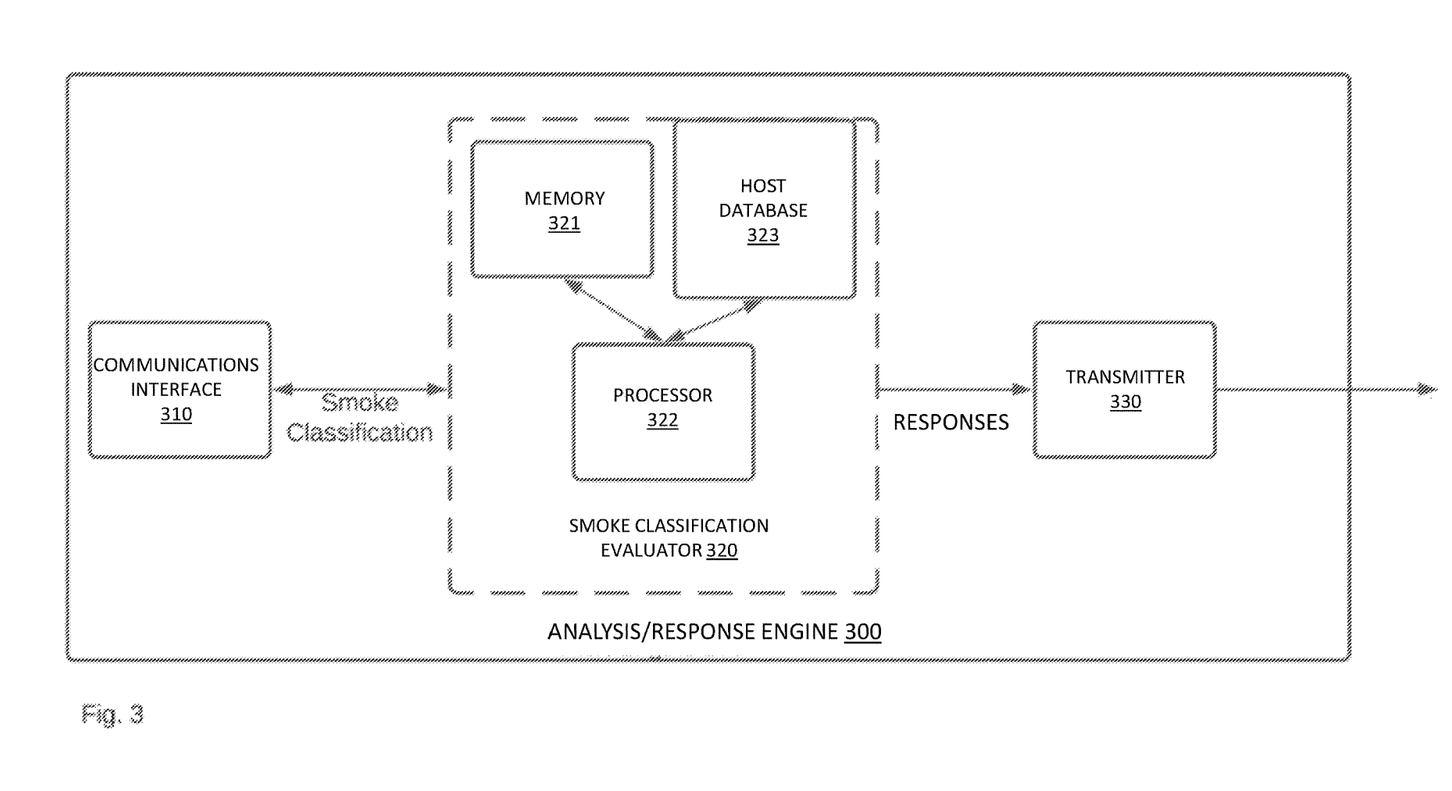
FIG. 3 is a block diagram of an example of an analysis/response engine constructed according to the principles of the disclosure.

FIG. 3 is a block diagram of an example of an analysis/response engine 300, such as analysis/response engine 170 of FIG. 1. The analysis/response engine 300 can take the form of a server, though other forms fall within the broad scope of the disclosure. The analysis/response engine 300 includes a communications interface 310, a smoke classification evaluator 320, and a transmitter 330.

The communications interface 310 can be a conventional interface for receiving and transmitting (i.e., communicating) data. The communications interface 310 is coupled to a network, e.g., the network 160 of FIG. 1, and is configured to receive from the network data/information from one or more air analyzers, such as air analyzers 140-1, 140-2. As discussed above, the data/information includes smoke classifications and can also include other data, such as sensor data. The analysis/response engine 300 is configured to receive, from the network via the communications interface 310, multiple communications (data/information) from multiple air analyzers over time. The air analyzers can be associated with many different monitored spaces having corresponding hosts.

The smoke classification evaluator 320 has one or more processor, represented by processor 322, and one or more memories or data storage, represented by memory 321. The memory 321 is configured to store operating instructions that direct the operation of the processor 322 when executed. The memory 321 can be a non-transitory memory. The operating instructions correspond to one or more algorithms that process the smoke classifications and generate responses, such as alerts, actions, or both. The smoke classification evaluator 320 further has host severity tuning database 323. The host severity tuning database 323, or simply host database, is configured to allow the smoke classification evaluator 320 to evaluate and characterize the at least one smoke classification to determine if the at least one smoke classification should merit a response. The host database 323 allows a customer, such as a host, to store their directions/preferences/instructions/selections for operating a monitoring system for smoking events, such as monitoring system 100. Default settings can also be used if no preferences or instructions are setup by a customer. The host database 323 can be part of the memory 321 or can be couplable via a network using the transmitter 330.

The host database 323 is configured to allow the smoke classification evaluator 320 (or processor 322 thereof) to determine the destination alert device that is appropriate for the alert (typically, but not necessarily, the alert device associated with the host of the property associated with the air analyzer that generated the smoke classification that gave rise to the alert). The host database 323 also includes selected types of classifications in which the owners prefer to be alerted about their respective monitored spaces. The different classification types allow different standards of what constitutes acceptable smoking types versus unacceptable smoking types to be applied to each air analyzer, and by extension to each space, separately. Accordingly, the communications interface 310 can receive a time stamp and an identifying number corresponding to the air analyzer. The smoke classification evaluator 320 can employ the time stamp to evaluate at least one smoke classification and employ the identifying number to identify the one or more designated destination alert devices. As such, the smoke classification evaluator 320 can evaluate by comparing multiple of the at least one smoke classification using time stamps associated therewith.

The analysis/response engine 300 further includes a transmitter 330 associated with the smoke classification evaluator 320. The transmitter 330 is configured to transmit an alert or operating commands for an action. The transmitter 330 can send an alert to one or more destination alert devices (e.g., the alert device 1 180 and/or the alert device 2 190 of FIG. 1). The alerts sent to different devices can be different. The alerts or subsequent alerts can include abatement actions that are being taken or that have occurred. The alerts can also indicate when smoking events have ceased. The operating commands can be sent to abatement devices.

Figure 4:
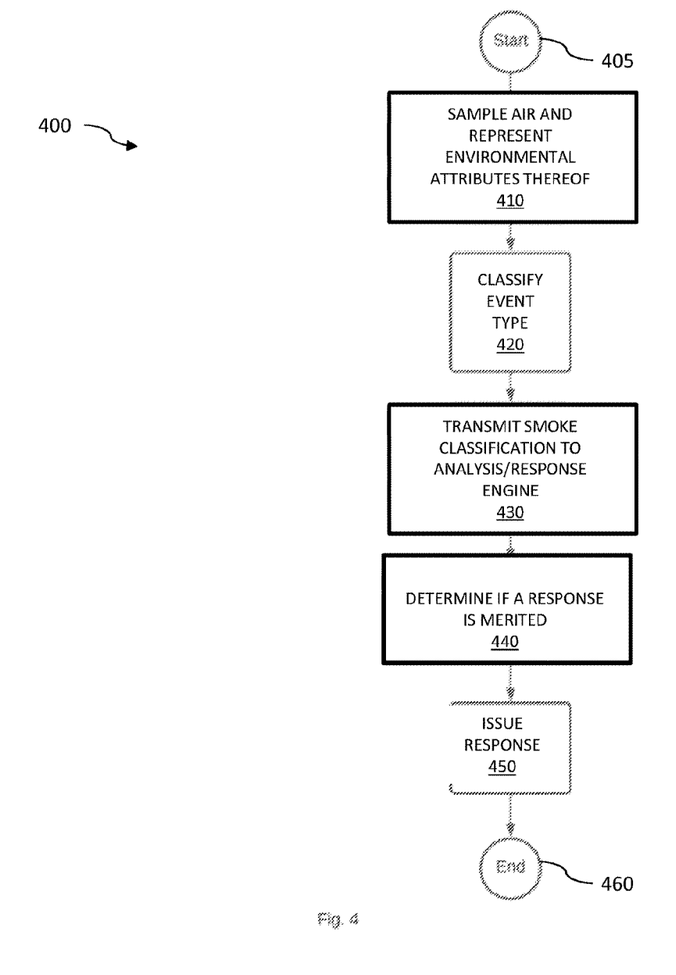
FIG. 4 is a flow diagram of an example of a method of classifying smoking events carried out according to the principles of the disclosure.

FIG. 4 is a flow diagram of an example of a method 400 of monitoring for smoking events that includes detecting and classifying smoking events according to the principles of the disclosure. A monitoring system, such as monitoring system 100, can be used to perform the steps of the method 400. The method 400 begins in a start step 405, when power is provided to an air analyzer using a power source contained in the air analyzer.

In step 410, air is sampled from the environment proximate the air analyzer. The sampled air can include a smoking event. The sampled air is processed by one or more sensors where different physical properties of air, referred to as environmental attributes, are determined according to the type of sensor. The physical properties can include particulate size, particulate average, concentration amount, etc. The sensors can generate electrical signals of different electrical properties, e.g., voltage, current and power, that represent the environmental attributes of the sampled air. The derived or generated electrical signals are raw signals or raw data that will be processed. A time stamp and an identifying number corresponding to the air analyzer may also be generated in step 410.

In a step 420, a smoke classification is generated from the raw signals that represent the environmental attributes. The smoke classification can be generated by comparing a processed signature determined from the raw signals to stored signatures. The stored signatures can be part of a data set of a model used for the classification. A general classification of smoking events and particular classifications of different types of smoking events can be provided.

In a step 430, the smoke classification is transmitted is transmitted for further processing. The smoke classification can be sent to an analysis/response engine for further processing. For example, the analysis/response engine 300. This usually involves first transmitting the smoke classification to a network, such as network 160.

In a step 440, smoke classification is received for processing, such as by an analysis/response engine. The smoke classification can be stored in a memory and processed in a processor, such as memory 321 and processor 322 of analysis/response engine 300. The processed signature used for the classification can also be stored in the memory.

Processing includes determining whether a response is merited based on one or more processed smoke classifications. A host database, such as host database 323, can be used to determine the type of response and when a response, such as an action or an alert, should be initiated or generated and to what or to whom the action command or (commands) or alert (or alerts) should be sent. Smoke classifications from more than one air analyzer can also be used for the processing. Additionally, data from other sensors or systems in addition to sensors of air analyzers can be used for the processing.

In a step 450, an action, an alert, or both is initiated or issued if the determination of the step 440 is positive. Multiple actions can be initiated and alerts can be sent to different abatement devices or customers. The method ends in an end step 460.

Those skilled in the art to which this application relates will appreciate that other and further additions, deletions, substitutions and modifications may be made to the described examples.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, a limited number of the exemplary methods and materials are described herein.

The flowchart and block diagrams in the figures illustrate the architecture, functionality, and operation of possible implementations of systems, methods and computer program products according to various examples of the present disclosure. In this regard, each block in the flowchart or block diagrams can represent a module, segment, or portion of code, which comprises one or more executable instructions for implementing the specified logical function(s). It should also be noted that, in some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

As will be appreciated by one of skill in the art, the disclosure or parts thereof may be embodied as a method, system, or computer program product. Accordingly, the features disclosed herein, or at least some of the features, may take the form of an entirely hardware example, an entirely software example (including firmware, resident software, micro-code, etc.) or an example combining software and hardware aspects all generally referred to herein as a "circuit" or "module." Some of the disclosed features may be embodied in or performed by various processors, such as digital data processors or computers, wherein the computers are programmed or store executable programs of sequences of software instructions to perform one or more of the steps of the methods. Thus, features or at least some of the features disclosed herein may take the form of a computer program product on a non-transitory computer-usable storage medium having computer-usable program code embodied in the medium. The software instructions of such programs can represent algorithms and be encoded in machine-executable form on non-transitory digital data storage media.

Thus, portions of disclosed examples may relate to computer storage products with a non-transitory computer-readable medium that have program code thereon for performing various computer-implemented operations that embody a part of an apparatus, device or carry out the steps of a method set forth herein. Non-transitory used herein refers to all computer-readable media except for transitory, propagating signals. Examples of non-transitory computer-readable media include, but are not limited to: magnetic media such as hard disks, floppy disks, and magnetic tape; optical media such as CD-ROM disks; magneto-optical media such as floptical disks; and hardware devices that are specially configured to store and execute program code, such as ROM and RAM devices. Examples of program code include machine code, such as produced by a compiler, and files containing higher level code that may be executed by the computer using an interpreter.

The processors discloses herein can be, for example, CPUs, GPUs, microprocessors, etc.

The terminology used herein is for the purpose of describing particular examples only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The disclosure provides different aspects. One aspect provides an air analyzer for detecting smoking events. In an example, the air analyzer includes: (1) Particulate Matter Sensor configured for high resolution and advanced particulate binning, (2) digital humidity and temperature sensor, and (3) digital multi-pixel gas sensor configured to derive momentary snap shots of gas levels, particulate counts and masses, temperature and humidity in order to quickly and accurately identify behaviors prohibited by a rental contract.

Another aspect provides a method for classification of smoking events. In an example the method includes: (1) deriving momentary snap shots of gas levels, particulate counts and masses, temperature and humidity in order to build fingerprints from air proximate to an air analyzer and (2) generating a classification of the type of smoking event proximate to the air analyzer using a classification model capable of approximating the type of smoking event.

Yet another aspect provides an analysis/response engine. In an example, the analysis/response engine includes: (1) a classification model coupled to a network and configured to receive therefrom at least one momentary snap shots of gas levels, particulate counts and masses, temperature and humidity in order to build fingerprints from air proximate an air analyzer, (2) classification evaluator having a processor, a memory and a host database, associated with the air analyzer and configured to evaluate the at least one momentary snap shots of gas levels, particulate counts and masses, temperature and humidity in order to build fingerprints from environmental attributes of the proximate air and determine should a response be issued (3) a transmitter, associated with the classification evaluator and configured to communicate a response such as transmitting an alert to a destination alert device or send action commands to an abatement device, and (4) makes historical data and analyses available for viewing through a dashboard, mobile app, and/or as a printable event report.

The disclosure provides the identification of certain particulates in the air resulting from smoking. Specifically, the disclosure relates to the classification of unique types of smoking events, such as, marijuana and nicotine, and providing responses that include generating alerts based on the classification of the previously described substance based on detection, time stamping and monitoring until the end of the smoking activity or to create a timely, automated intervention to end or abate the smoke activity.

Those skilled in the art to which this application relates will appreciate that other and further additions, deletions, substitutions and modifications may be made to the described examples.

Each of the aspects of the Summary may have one or more of the elements from the following dependent claims in combination.

What is claimed is:

1. An air analyzer, comprising:
multiple sensors including one or more of a digital multi-pixel gas sensor, a digital humidity and temperature sensor, or a particulate matter sensor, wherein each of the multiple sensors is configured to obtain a sample of air and derive therefrom an environmental attribute, wherein the environmental attributes provide a signature of the sampled air; and
a processor to classify a smoking event by comparing the signature of sampled air to signatures of a classification model, generate a time stamp associated with the smoke event and an identifying number corresponding to the air analyzer, and provide the time stamp and the identifying number for determining if a response should be issued or what type of response should be issued, wherein the response includes an action and sending commands for the action to at least one abatement device for the action.

2. The air analyzer as recited in claim 1, wherein the signature of sampled air provides a momentary representation of measurements obtained by the multiple sensors.

3. The air analyzer as recited in claim 1, wherein the signature of sample air is associated with a time window and the processor is further configured to consider the time window when performing the comparing.

4. The air analyzer as recited in claim 1, wherein the smoke classification is a number based on at least two of the environmental attributes.

5. The air analyzer as recited in claim 4, wherein the smoke classification is based on perceived levels of TVOC, $CO_2$, and NOX.

6. The air analyzer as recited in claim 5, wherein the smoke classification is further based on a time window.

7. The air analyzer as recited in claim 1, further comprising a memory that stores the classification model.

8. The air analyzer as recited in claim 1, further comprising a transceiver configured to transmit the smoke classification, the time stamp, and the identifying number to a network.

9. A method of detecting smoking events, comprising:
sampling air using one or more sensors;
determining presence of a trigger event and a termination event from the sampled air;
determining smoking events from the sampled air by comparing a time window between the trigger and termination events to time windows of modelled smoking events;
comparing representations of the sampled air with signature models for the determined smoking events;
classifying the smoking events based on the comparing;
generating a time stamp for each of the smoking events;
providing the multiple smoke classifications for comparison, using at least the time stamps associated therewith, to evaluate whether at least one of the multiple smoke classifications should merit a response, wherein the response includes an action;

generating commands for the action; and transmitting the commands to at least one abatement device for the action.

10. The method as recited in claim 9 wherein the one or more sensors include a digital multi-pixel gas sensor, a digital humidity and temperature sensor, or a particulate matter sensor.

11. The method as recited in claim 9, further comprising representing the sampled air using outputs from the sensors and using the outputs for determining the trigger and termination events.

12. The method as recited in claim 9, further comprising generating an identifying number corresponding to an air analyzer that performs the sampling.

13. The method as recited in claim 9 wherein the trigger and termination events are based on thresholds.

14. The method as recited in claim 9, wherein the providing includes transmitting the multiple smoke classifications and the time stamps associated therewith to a network.

15. The method as recited in claim 9, wherein the one or more sensors are integrated with an air analyzer and the method further includes providing power to the air analyzer via a wall outlet.

16. An analysis/response engine, comprising:
a communications interface couplable to a network and configured to receive therefrom at least one smoke classification from an air analyzer, a time stamp associated with said at least one smoke classification, and an identifying number corresponding to said air analyzer;
a processor associated with a host database and configured to evaluate said at least one smoke classification using data from said host database to determine if said at least one smoke classification should merit a response, and employ said time stamp and said identifying number for determining if a response should be issued and what type of response to issue when a response is merited; and
a transmitter, associated with said processor and configured to issue the response, wherein the response includes an action and the processor is further configured to generate commands for the action and determine at least one abatement device for the action, and the transmitter is configured to transmit the commands to the at least one abatement device.

17. The analysis/response engine as recited in claim 16, wherein the response further includes an alert and the processor is configured to generate the alert and determine at least one destination device for the alert, and the transmitter is configured to transmit the alert to the at least one destination device.

18. The analysis/response engine as recited in claim 16, wherein the at least one abatement device includes a fan.

19. The analysis/response engine as recited in claim 16, wherein the at least one abatement device includes an HVAC system.

20. The analysis/response engine as recited in claim 16, wherein said host database includes instructions or settings corresponding to said air analyzer.

21. The analysis/response engine as recited in claim 20, wherein said instructions or settings differ for different air analyzers.

22. The analysis/response engine as recited in claim 16, wherein said evaluating comprises comparing multiple smoke classifications using time stamps associated therewith.

23. The analysis/response engine as recited in claim 17, wherein said destination alert device is a mobile device.

24. An air analyzer, comprising:
one or more sensors configured to identify environmental attributes in air; and
one or more processors to perform operations including determining multiple smoke events based on the environmental attributes, classifying the multiple smoke events, and providing the multiple smoke classifications for comparison, using time stamps associated therewith, to evaluate whether at least one of the multiple smoke classifications should merit a response, wherein the response includes an action and sending commands for the action to at least one abatement device for the action.

25. The air analyzer as recited in claim 24, wherein the multiple smoke events include different types of smoking events.

26. The air analyzer as recited in claim 24, including multiple sensors, wherein the multiple sensors include a vibration sensor, a digital gas sensor, a digital temperature sensor, and a particulate matter sensor.

27. The air analyzer as recited in claim 24, wherein one of the environmental attributes corresponds to noise.

* * * * *